United States Patent [19]

Nafziger et al.

[11] 4,064,157

[45] Dec. 20, 1977

[54] STABILIZATION OF POLYISOCYANATES AGAINST DISCOLORATION

[75] Inventors: John L. Nafziger; John M. Motes, both of Lake Jackson, Tex.

[73] Assignee: The Dow Chemical Company, Midland, Mich.

[21] Appl. No.: 671,201

[22] Filed: Mar. 29, 1976

[51] Int. Cl.$^2$ .......................................... C07C 119/042
[52] U.S. Cl. ............................................... 260/453 SP
[58] Field of Search ............... 260/453 SP, 473 S, 961

[56] References Cited

U.S. PATENT DOCUMENTS

| | | | |
|---|---|---|---|
| 2,950,307 | 8/1960 | France et al. | 260/453 |
| 2,957,903 | 10/1960 | Spiegler | 260/453 |
| 3,285,855 | 11/1966 | Dexter et al. | 260/473 X |
| 3,367,870 | 2/1968 | Spivack | 260/45.95 D |

*Primary Examiner*—Dolph H. Torrence
*Attorney, Agent, or Firm*—James G. Carter

[57] ABSTRACT

Polyisocyanates are stabilized against discoloration by the addition of certain hindered phenols such as o,o-di-n-octadecyl-3,5-di-tert-butyl-4-hydroxyl benzyl phosphonate.

18 Claims, No Drawings

STABILIZATION OF POLYISOCYANATES AGAINST DISCOLORATION

The present invention relates to polyisocyanates stabilized against discoloration and a process for such stabilization and more particularly it relates to toluene diisocyanate stabilized with certain hindered phenols.

Polyisocyanates have been stabilized against oxidative degradation and discoloration with phenolic compounds as described in U.S. Pat. Nos. 2,950,307; 3,149,139; 3,226,411 and 3,715,381.

Reaction products of polyether polyols and polyisocyanates have been stabilized against oxidation and discoloration by the use of a synergistic combination of phenolic compounds and phosphoric acid.

It has now been unexpectedly discovered that certain phenolic compounds are effective in stabilizing polyisocyanates against discoloration.

It has also been unexpectedly discovered that certain phenolic compounds act synergistically, at low levels, with organic phosphites.

The polyisocyanates are stabilized with from about 20 ppm to about 2500 ppm, preferably from about 50 ppm to about 500 ppm by weight based upon the polyisocyanate of a hereinafter described phenolic compound.

The polyisocyanates are also stabilized against discoloration according to the present invention by the addition thereto of from about 10 ppm to about 2500 ppm, preferably from about 25 ppm to about 250 ppm based upon the polyisocyanate of a mixture of one or more of the hereinafter described phenolic compounds and an organic phosphite in an equivalent ratio of phenolic compound to organic phosphite of from about 0.01:1 to about 10:1, preferably from about 0.35:1 to about 1.45:1.

Suitable polyisocyanates which can be stabilized against discoloration include aromatic, aliphatic, and cycloaliphatic polyisocyanates such as, for example, ethylene diisocyanate
tetramethylene diisocyanate
hexamethylene diisocyanate
decamethylene diisocyanate
cyclohexyl diisocyanate
4,4′-methylenebis(cyclohexyl isocyanate)
m-phenylene diisocyanate
p-phenylene diisocyanate
tolylene-2,4-diisocyanate
tolylene-2,6-diisocyanate
4,4′-methylenebis(phenyl isocyanate)
tolylene-2,4,6-triisocyanate
monochlorobenzene-2,4,6-triisocyanate
2,3,5,6-tetramethyl-p-phenylene diisocyanate
xylene diisocyanate
isophorone diisocyanate mixtures thereof and the like.

Suitable phenolic compounds which can be employed to stabilize organic polyisocyanates against discoloration include, for example, o,o-di-n-octadecyl-3,5-di-tert-butyl-4-hydroxy benzyl phosphonate,
octadecyl-3,5-di-tert-butyl-4-hydroxyhydrocinnamate,
tetrakis(methylene(3,5-di-tert-butyl-4-hydroxyhydrocinnamate))methane,
bis(2-(4-hydroxy-3,5-di-tert-butylphenyl)ethyl)sulfide
mixtures thereof and the like.

Suitable organic phosphites which can be employed to stabilize organic polyisocyanates against discoloration include, for example, triphenyl phosphite
diphenylisodecyl phosphite
trisnonylphenyl phosphite
triisodecyl phosphite
trilauryl phosphite mixtures thereof and the like.

Organic polyisocyanates can be stabilized in accordance to the present invention by merely admixing the polyisocyanates with the stabilizer component or components. When an organic phosphite is employed in combination with the phenolic compound, it is preferred to add the stabilizer composition to a polyisocyanate which has previously been distilled in the presence of at least about 25 ppm, preferably from about 50 to about 600 ppm based on the weight of the polyisocyanate of an organic phosphite.

The following examples are illustrative of the present invention, but are not to be construed as to limiting the scope thereof in any manner.

In the examples, the following stabilizer designations were utilized.

STABILIZER A was triphenyl phosphite.
STABILIZER B was o,o-di-n-octadecyl-3,5-di-tert-butyl-4-hydroxybenzylphosphonate.
STABILIZER C was tetrakis(methylene(3,5-di-tert-butyl-4-hydroxyhydrocinnamate))methane.
STABILIZER D was bis(2-(4-hydroxy-3,5-di-tert-butylphenyl) ethyl)sulfide.
STABILIZER E was octadecyl-2,4-di-tert-butyl-4-hydroxyhydrocinnamate.
STABILIZER F was 2,6-di-tert-butyl-4-methylphenol.

EXAMPLE 1

The stability of an 80/20 mixture of 2,4-/2,6-toluene diisocyanate was checked at various concentrations employing stabilizers A and B alone and 50% by weight mixtures of stabilizers A and B and stabilizers A and C. The various mixtures were stored in the presence of air for 97 days at 20°–30° C. The results are given in Table I.

TABLE I

| | APHA Color Total Quantity of Stabilizer | | | | |
|---|---|---|---|---|---|
| Stabilizer System | 63 ppm | 125 ppm | 250 ppm | 500 ppm | 1000 ppm |
| Stabilizer A | >100 | >100 | >100 | >100 | 100 |
| Stabilizer B | 90 | 15 | 15 | 20 | 25–30 |
| 50 wt. % A + 50 wt. % B[1] | 35 | 20 | 15 | 15 | 15–20 |
| 50 wt. % A + 50 wt. % C[2] | 20 | 15–20 | 15 | 10 | 10 |

[1]72 equivalent % A and 28 equivalent % B
[2]49 equivalent % A and 51 equivalent % C

EXAMPLE 2

The effect of various stabilizers in preventing discoloration of an 80/20 mixture of 2,4-/2,6-toluene diisocyanate in the presence of air and carbon steel and in the absence of light was determined by storing the stabilized samples for 109 days at 21°–41° C. The results are given in Table II. An unstabilized sample had a color of >100 after the test period.

TABLE II

| | Test Number | | | | | | | | | |
|---|---|---|---|---|---|---|---|---|---|---|
| | 1 | 2 | 3 | 4 | 5 | 6 | 7 | 8 | 9 | 10 |
| Stabilizer A | | | | | | | | | | |
| ppm[1] | 1000 | | | | | 500 | 500 | 500 | 500 | 500 |
| meqpkg[2] | 3.23 | | | | | 1.61 | 1.61 | 1.61 | 1.61 | 1.61 |
| Stabilizer B | | | | | | | | | | |
| ppm | | 1000 | | | | 500 | | | | |
| meqpkg | | 1.24 | | | | 0.62 | | | | |
| Stabilizer C | | | | | | | | | | |
| ppm | | | 1000 | | | | 500 | | | |
| meqpkg | | | 3.4 | | | | 1.7 | | | |
| Stabilizer D | | | | | | | | | | |
| ppm | | | | 1000 | | | | 500 | | |
| meqpkg | | | | 4.02 | | | | 2.01 | | |
| Stabilizer E | | | | | | | | | | |
| ppm | | | | | | | | | 500 | |
| meqpkg | | | | | | | | | 0.94 | |
| Stabilizer F | | | | | | | | | | |
| ppm | | | | | 1000 | | | | | 500 |
| meqpkg | | | | | 4.54 | | | | | 2.27 |
| APHA Color | 25 | 20 | 70–80 | 70 | 55 | 15–20 | 35 | 20 | 20 | 20–25 |

[1]parts per million parts by weight of toluene diisocyanate.
[2]milliequivalents per kilogram of toluene diisocyanate.

EXAMPLE 3

The stability of an 80/20 mixture of 2,4-/2,6-toluene diisocyanate was checked at various concentrations with stabilizers A and B and with a 50% mixture and also with a 50% mixture of stabilizers A and C. The stabilizers were added to portions of the toluene diisocyanate which had just previously been distilled in the presence of 600 ppm of stabilizer A. The distillate did not, by gc analysis contain any residual quantities of stabilizer A. The results after storing in the presence of air for 90 days at 21°–25° C are given in Table III.

TABLE III

| | APHA Color Total Quantity of Stabilizer | | | | |
|---|---|---|---|---|---|
| Stabilizer System | 63 ppm | 125 ppm | 250 ppm | 500 ppm | 1000 ppm |
| Stabilizer A | 100 | 100 | 100 | 75 | 70 |
| Stabilizer B | 35–40 | 35–40 | 35–40 | 30 | 50 |
| 50 wt. % A + 50 wt. % B[1] | 40 | 30 | 35 | 30 | 40 |
| 50 wt. % A + 50 wt. % C[2] | 35 | 35 | 35 | 40 | 25–30 |

[1]72 equivalent % A + 28 equivalent % B
[2]49 equivalent % A + 51 equivalent % C

We claim:

1. A polyisocyanate containing as a stabilizer against discoloration, from about 20 to about 2500 ppm of a stabilizer selected from the group consisting of
   1. o,o-di-n-octadecyl-3,5-di-tert-butyl-4-hydroxybenzylphosphonate,
   2. tetrakis(methylene(3,5-di-tert-butyl-4-hydroxyhydrocinnamate))methane,
   3. bis(2- (4-hydroxy-3,5-di-tert-butylphenyl) ethyl)-sulfide,
   4. octadecyl-3,5-di-tert-butyl-4-hydroxy-hydrocinnamate, and
   5. mixtures thereof.

2. The composition of claim 1 wherein the polyisocyanate is toluene diisocyanate and the stabilizer is present in quantities of from about 50 ppm to about 500 ppm.

3. The composition of claim 2 wherein the polyisocyanate is an 80/20 mixture of 2,4-/2,6-toluene diisocyanate.

4. The process for preparing a polyisocyanate resistant to discoloration upon storage which comprises distilling said polyisocyanate in the presence of at least about 25 ppm of an organic phosphite selected from the group consisting of
   1. triphenyl phosphite,
   2. diphenylisodecyl phosphite,
   3. trisononylphenyl phosphite,
   4. trilauryl phosphite, and
   5. mixtures thereof;
and adding to the resultant distillate a stabilizer selected from the group consisting of
   1. o,o-di-n-octadecyl-3,5-di-tert-butyl-4-hydroxybenzylphosphonte,
   2. tetrakis(methylene(3,5-di-tert-butyl-4-hydroxyhydrocinnamate))methane,
   3. bis(2-(4-hydroxy-3,5-di-tert-butylphenyl)ethyl)sulfide,
   4. octadecyl-3,5-di-tert-butyl-4-hydroxyhydrocinnamate, and
   5. mixtures thereof; and
wherein said stabilizer is employed in quantities of from about 20 ppm to about 250 ppm.

5. The process of claim 4 wherein the polyisocyanate is toluene diisocyanate which is distilled in the presence of from about 50 ppm to about 600 ppm of triphenyl phosphite and the stabilizer is present in quantities of from about 50 ppm to about 500 ppm.

6. The process of claim 5 wherein the polyisocyanate is an 80/20 mixture of 2,4-/2,6-toluene diisocyanate.

7. A polyisocyanate containing as a stabilizer against discoloration from about 10 ppm to about 250 ppm of a mixture comprising
A. an organic phosphite selected from the group consisting of
   1. triphenyl phosphite,
   2. diphenylisodecyl phosphite,
   3. trisononylphenyl phosphite,
   4. triisodecyl phosphite,
   5. trilauryl phosphite, and
   6. mixtures thereof; and
B. a member of the group consisting of
   1. o,o-di-n-octadecyl-3,5-di-tert-butyl-4-hydroxybenzylphosphonate,
   2. tetrakis(methylene(3,5-di-tert-butyl-4-hydroxyhydrocinnamate))methane,
   3. bis(2-(4-hydroxy-3,5-di-tert-butylphenyl)ethyl)sulfide,
   4. octadecyl-3,5-di-tert-butyl-4-hydroxyhydrocinnamate, and
   5. mixtures thereof; and wherein the equivalent ratio of B:A is from about 0.01:1 to about 10:1.

8. The composition of claim 7 wherein the polyisocyanate is toluene diisocyanate and the stabilizer is present in quantities of from about 25 ppm to about 250 ppm.

9. The composition of claim 8 wherein the polyisocyanate is an 80/20 mixture of 2,4-/2,6-toluene diisocyanate.

10. The composition of claim 9 wherein the stabilizer mixture is in an equivalent ratio of (B):(A) of from about 0.35:1 to about 1.45:1.

11. The composition of claim 10 wherein the stabilizer is a mixture of triphenyl phosphite and Component (B-2).

12. The composition of claim 10 wherein the stabilizer is a mixture of triphenyl phosphite and Component (B-3).

13. A process for preparing a polyisocyanate resistant to discoloration upon storage which comprises distilling said polyisocyanate in the presence of at least about 25 ppm of an organic phosphite and adding to the resultant distillate a stabilizer mixture comprising A. an organic phosphite selected from the group consisting of
  1. triphenyl phosphite,
  2. diphenylisodecyl phosphite,
  3. trisnonylphenyl phosphite,
  4. triisodecyl phosphite,
  5. trilauryl phosphite, and
  6. mixtures thereof; and B. a member of the group consisting of
  1. o,o-di-n-octadecyl-3,5-di-tert-butyl-4-hydroxybenzylphosphonate,
  2. tetrakis(methylene(3,5-di-tert-butyl-4-hydroxyhydrocinnamate))methane,
  3. bis(2-(4-hydroxy-3,5-di-tert-butylphenyl)ethyl)sulfide,
  4. octadecyl-3,5-di-tert-butyl-4-hydroxyhydrocinnamate, and
  5. mixtures thereof; and wherein the equivalent ratio of (B) : (A) is from about 0.01:1 to about 10:1.

14. The composition of claim 13 wherein the polyisocyanate is toluene diisocyanate and the stabilizer is present in quantities of from about 25 ppm to about 250 ppm.

15. The composition of claim 14 wherein the polyisocyanate is an 80/20 mixture of 2,4-/2,6-toluene diisocyanate.

16. The composition of claim 15 wherein the stabilizer mixture is in an equivalent ratio of (B):(A) of from about 0.35:1 to about 1.45:1.

17. The composition of claim 16 wherein the stabilizer is a mixture of triphenyl phosphite and Component (B-2).

18. The composition of claim 16 wherein the stabilizer is a mixture of triphenyl phosphite and Component (B-3).

* * * * *